US009977015B2

(12) United States Patent
Sing et al.

(10) Patent No.: US 9,977,015 B2
(45) Date of Patent: May 22, 2018

(54) SYSTEMS AND METHODS FOR DETECTING MOLECULAR INTERACTIONS USING MAGNETIC BEADS

(71) Applicant: Massachusetts Institute of Technology, Cambridge, MA (US)

(72) Inventors: Charles E. Sing, Cambridge, MA (US); Joshua P. Steimel, Cambridge, MA (US); Alfredo Alexander-Katz, Cambridge, MA (US)

(73) Assignee: Massachusetts Institute of Technology, Cambridge, MA (US)

( * ) Notice: Subject to any disclaimer, the term of this patent is extended or adjusted under 35 U.S.C. 154(b) by 628 days.

(21) Appl. No.: 14/401,493

(22) PCT Filed: May 15, 2013

(86) PCT No.: PCT/US2013/041211
§ 371 (c)(1),
(2) Date: Nov. 14, 2014

(87) PCT Pub. No.: WO2013/173497
PCT Pub. Date: Nov. 21, 2013

(65) Prior Publication Data
US 2015/0147821 A1 May 28, 2015

Related U.S. Application Data

(60) Provisional application No. 61/647,265, filed on May 15, 2012.

(51) Int. Cl.
*G01N 33/543* (2006.01)
*G01N 27/74* (2006.01)
*B01L 3/00* (2006.01)

(52) U.S. Cl.
CPC ..... *G01N 33/54326* (2013.01); *G01N 27/745* (2013.01); *B01L 3/502761* (2013.01)

(58) Field of Classification Search
None
See application file for complete search history.

(56) References Cited

U.S. PATENT DOCUMENTS

| | | | |
|---|---|---|---|
| 2003/0044992 A1* | 3/2003 | Chao | B01L 3/502776 436/52 |
| 2004/0132122 A1* | 7/2004 | Banerjee | B01J 19/0046 435/7.92 |
| 2005/0009099 A1* | 1/2005 | Lockhart | C12Q 1/485 435/7.1 |
| 2007/0290683 A1* | 12/2007 | Ikeda | B82Y 15/00 324/260 |
| 2008/0011977 A1* | 1/2008 | Atwood | B82Y 15/00 252/62.51 R |
| 2008/0206104 A1* | 8/2008 | Prins | G01N 27/745 422/82.01 |
| 2014/0255976 A1* | 9/2014 | Chang | C07K 16/30 435/30 |

FOREIGN PATENT DOCUMENTS

| | | | |
|---|---|---|---|
| WO | 2005111596 | 11/2005 | |
| WO | 2006134546 | 12/2006 | |
| WO | WO-2009037636 A1 * | 3/2009 | ........... G01N 27/745 |
| WO | 2012142179 | 10/2012 | |

OTHER PUBLICATIONS

Search Report and Written Opinion dated Sep. 12, 2013 for PCT Application No. PCT/US2013/041211 (13 pages).
Kim et al., "Magnetic Force-Based Multiplexed Immunoassay Using Superparamagnetic Nanoparticles in Microfluidic Channel," Lab Chip, 2005, 5:657-664.
Sandhu et al., "Synthesis and Applications of Magnetic Nanoparticles for Biorecognition and Point of Care Medical Diagnostics," Nanotechnoology, 2010, 21:442991, 22 pages.
Gijs et al., "Microfluidic Applications of Magnetic Particles for Biological Analysis and Catalysis," Chem. Rev., 2010, 110:1518-1563.
Florin et al., "Adhesion Forces Between Individual Ligand-Receptor Pairs," Science, 1994, 264:415-417.
Genzer et al., "Surface-Bound Soft Matter Gradients," Lanmuir, 2008, 24:2294-2317.
Mair et al., "Highly Controllable Near-Surface Swimming of Magnetic Janus Nanorods: Application to Payload Capture and Manipulation," J. Phys. D: Appl. Phys., 2011, 44:125001 (9 pages).
Morgenthaler et al., "A Simple, Reproducible Approach to the Preparation of Surface-Chemical Gradients," American Chemical Society, 2003, 19(25):10459-10462.
Morgenthaler et al. "Surface-Chemical and -Morphological Gradients," Soft Matter, 2008, 4:419-434.
Morimoto et al., "Tumbling Motion of Magnetic Particles on a Magnetic Substrate Induced by a Rotational Magnetic Field," Physical Review, 2008, E 78, 021403-1-021403-7.
Sing et al., "Controlled Surface-Induced Flows from the Motion of Self-Assembled Colloidal Walkers," PNAS, 2010, 107(2):535-540.
Steimel et al., "Artificial Tribotatic Microscopic Walkers: Walking Based on Friction Gradients," PRL, 2014, 113:178101-1-178101-5.
Tierno et al., "Controlled Propulsion in Vicious Fluids of Magnetically Actuated Colloidal Doublets," Physical Review E, 2010, 81:011402-1-011402-9.

(Continued)

*Primary Examiner* — Gary Counts
(74) *Attorney, Agent, or Firm* — Eversheds Sutherland (US) LLP

(57) ABSTRACT

Systems and methods are provided for detecting or measuring binding affinity between different compositions. The methods include contacting one or more magnetic beads having a surface including a first composition with a substrate having a surface including a second composition; applying a rotating magnetic field to the one or more magnetic beads effective to cause the one or more magnetic beads to move across the surface of the substrate; measuring the movement of the one or more magnetic beads across the substrate surface to determine a translational velocity; and determining a binding affinity between the first and second compositions from the translational velocity.

21 Claims, 10 Drawing Sheets

(56) References Cited

OTHER PUBLICATIONS

Tierno et al., "Controlled Swimming in Confined Fluids of Magnetically Actuated Colloidal Rotors," PRL, 2008, 101:218304-1-218304-4.
Tierno et all., "Magnetically Actuated Colloidal Microswimmers," J. Phys. Chem., 2008, 112:16525-16528.

* cited by examiner

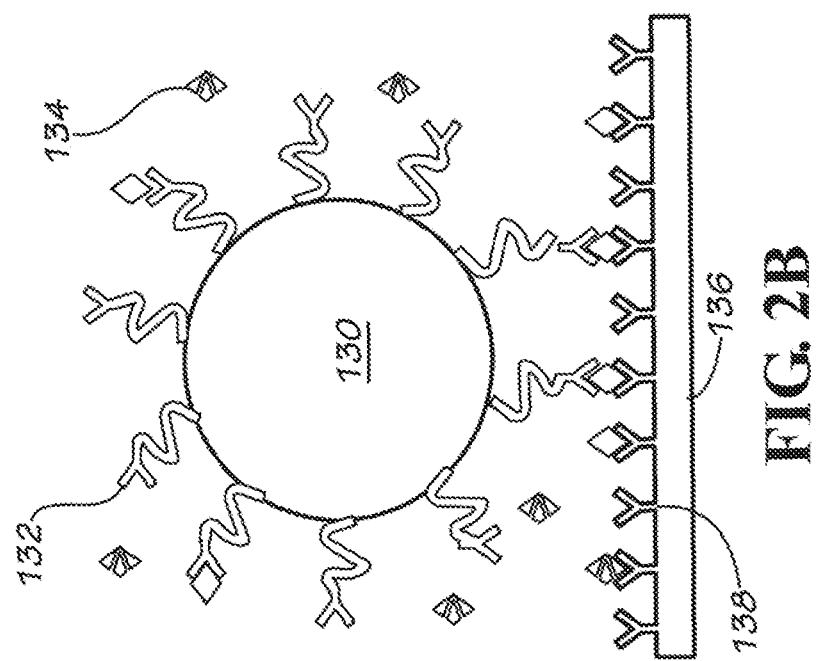
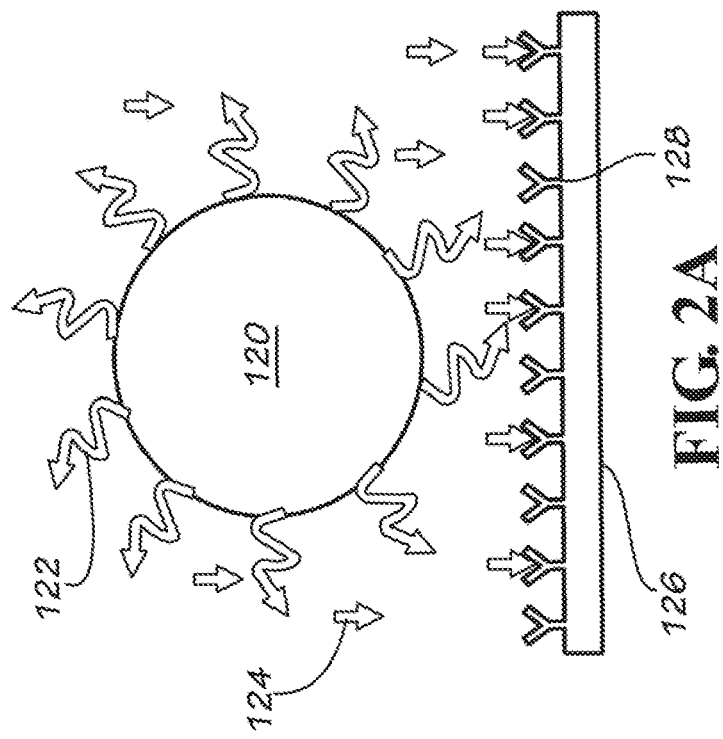

SYSTEMS AND METHODS FOR DETECTING MOLECULAR INTERACTIONS USING MAGNETIC BEADS

CROSS-REFERENCE TO RELATED APPLICATIONS

This application claims priority to U.S. Provisional Patent Application No. 61/647,265, filed May 15, 2012, which is incorporated herein by reference.

BACKGROUND

Embodiments of the present application relate to systems and methods for detection of binding between biological and/or synthetic (organic or inorganic) molecules. In particular, the systems and methods provided herein enable measurement of the binding affinity between different molecules in both label-free and label-based modalities, as well as automated detection of gradients in the immobilized species.

The detection of binding between two different biological molecules has revolutionized multiple areas of healthcare and diagnostics. There currently are a multitude of schemes to detect the binding between two molecules, which can be subdivided as being label-free or label-based.

Label-based detection is widely used in protein microarrays due to the common availability of reagents and simple instrument requirements. However, these labeling strategies often alter both surface characteristics and natural activities of the query molecule. Such label-based techniques include chromogenic detection, fluorescent-based detection, radioactive labeling, and chemiluminescense. In all of these techniques, one of the molecule-types is immobilized on a surface (the "substrate molecule"). Subsequently, another molecule (labeled or unlabeled, the "target molecule") is allowed to interact with the substrate. To determine if the pair of molecules bind, a secondary molecule that also binds the target molecule may be introduced, and such secondary molecule may be labeled with a motif, non-limiting examples of which include fluorescent tags or substrates on which enzymes can change colors. Thus, the motif provides a means to evaluate whether an interaction has occurred, for example, by optically measuring the signal coming from the sample. If the target molecule is independently labeled, however, the secondary molecule is unnecessary. Because each of these techniques typically requires multiple wash cycles, label-based techniques generally are time-consuming. A common label-based technique is an ELISA, which can also be done as a function of time to provided kinetic information of the binding reactions.

Label-free techniques, unlike label-based techniques, are capable of directly detecting if a target molecule is bound to the substrate molecule without the use of a secondary molecule with a motif. There are multiple label-free techniques, the most common of which are either optical (i.e., using surface plasmon resonances (SPR)) or mechanical (i.e., using a quartz microbalance (QM) to detect changes in the vibration resonant frequency).

SPR techniques measure the change in the thickness or refractive index of biomaterials at the interface between metal surfaces, usually a thin gold film (50-100 nm) coated on a glass slide in an ambient medium. The test proteins are immobilized on the gold film, an unlabeled query protein is added, and the change in the angle of reflection of light caused by binding of the query protein to the immobilized protein is measured to characterize biomolecular interactions in real-time. The angle at which the minimum intensity of the reflected light is obtained is directly related to the amount of biomolecules bound to the gold film.

Variations of this technique and alternative optical techniques also are known, but all rely on the change of the effective index of refraction of the substrate upon binding of the target molecules to the substrate. Acoustic biosensors also allow for the label-free detection of molecules and analysis of binding events. The acoustic biosensors generally are based on quartz crystal resonators, commonly found in electronic devices such as watches, computers and televisions. In such systems, there is a linear relationship between the mass adsorbed to the surface and the resonant frequency of the crystal in air, vacuum, or liquids.

Although existing label-based and label-free techniques provide methods for evaluating interactions between molecules, these techniques are usually time-consuming, complex, and lack the necessary sensitivity to detect both specific and unspecific-binding. Thus, there remains a need for simplified and versatile systems and methods for evaluating molecular binding.

SUMMARY

Embodiments described herein address the foregoing needs by providing systems and methods for detecting or measuring the binding affinity between different materials, such as different molecules.

In one aspect, a method is provided for detecting or measuring binding affinity between different substrates. In embodiments, the method includes (i) contacting one or more magnetic beads having a surface which comprises a first composition with a substrate having a surface which comprises a second composition, wherein the first composition differs from second composition; (ii) applying a rotating magnetic field to the one or more magnetic beads effective to cause the one or more magnetic beads to move across the surface of the substrate; (iii) measuring the movement of the one or more magnetic beads across the substrate surface to determine a translational velocity; and (iv) determining a binding affinity between the first and second compositions from the translational velocity. The step of determining the binding affinity generally includes determining the affinity between the surface of the magnetic beads and the surface of the substrate. In a preferred embodiment, the step of measuring the translational velocity of the one or more magnetic beads is performed using optical microscopy.

In another aspect, a system is provided for detecting and measuring the binding affinity of different substrates. In one embodiment, the system includes a magnetic field source configured to apply a rotating magnetic field to one or more magnetic beads in contact with a substrate to cause the one or more magnetic beads to move across the substrate. An optical detector is configured to detect or measure the translational velocity of the movement of the one or more magnetic beads across the substrate surface. A processor may be coupled to the optical detector for calculating the binding affinity between a first composition on the surface of the one or more magnetic beads and a second composition on the surface of the substrate.

These and other aspects and embodiments of the disclosed methods are described more fully in the detailed description.

BRIEF DESCRIPTION OF THE DRAWINGS

FIGS. 2A and 2B are schematic illustrations of free molecules added to magnetic beads in contact with a substrate capable of masking (2A) the substrate molecules to reduce binding between the bead and substrate molecules or increasing (2B) the interactions between the bead and substrate molecules.

DETAILED DESCRIPTION

Simple, versatile, and robust systems and methods are provided for detecting and measuring the binding affinity between different materials, such as different types of molecules. Advantageously, the systems and methods described herein can be used with either label-free or label-based modalities for quantitative analysis of binding affinity, and are not sensitive to unspecific binding to the substrate unless the unspecific binding directly affects the primary target-substrate interaction and secondary-substrate interaction being probed.

Generally described, systems and methods are provided to detect or measure binding affinity between different compositions by applying a rotating magnetic field to one or more magnetic beads having a surface comprising a first composition in contact with a substrate having a surface comprising a mobile or immobilized second type of composition. The rotating magnetic field is effective to cause the one or more magnetic beads to move across the surface of the substrate, enabling the translational velocity of the one or more magnetic beads to be measured. From the translational velocity, the binding affinity of the one or more magnetic beads between the first and second compositions can be detected and quantified. For example, the difference between the translational velocity of the one or more magnetic beads and that of the one or more controls can indicate the binding affinity between the first and second compositions.

In embodiments of the methods and systems described herein, the surfaces of the magnetic bead and the substrate can have essentially any composition, though generally the composition of the magnetic bead surface differs from that of the substrate across which the magnetic bead translates. For example, in embodiments the first composition comprises one or more of a first type of molecule and the second composition comprises one or more of a second type of molecule. In some embodiments, one or both surfaces can include a complex system, such as (biological) cells. For simplicity, embodiments of the methods and systems described herein primarily are described with reference to molecules on the surfaces of the magnetic beads and substrate; however, it should be appreciated that essentially any other composition may be used where reference is made to the molecule(s) (i.e., bead molecules, substrate molecules, or free molecules).

As used herein, the "binding affinity" refers to the interaction between two or more different surface materials, such as two or more different molecules. The binding affinity can be characterized either qualitatively or quantitatively. For example, a quantitative evaluation of the binding affinity may include evaluation of the kinetics of the molecular interactions by calculation of the binding constant (also referred to as the kinetic adsorption constant or kinetic association constant) from the translational velocity.

Figure 1B:
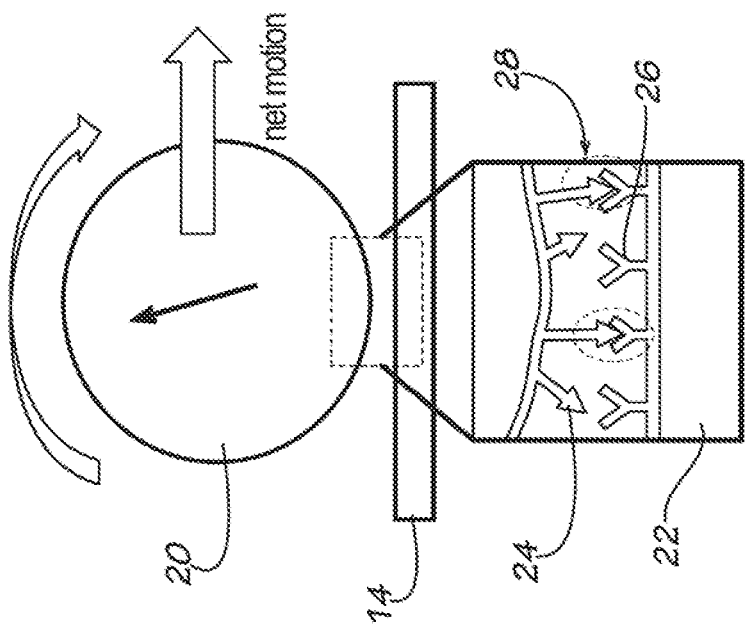
FIGS. 1A and 1B are schematic illustrations of a rotating magnetic bead in contact with a substrate without (1A) and with (1B) binding between the bead and substrate molecules.
Figure 1A:
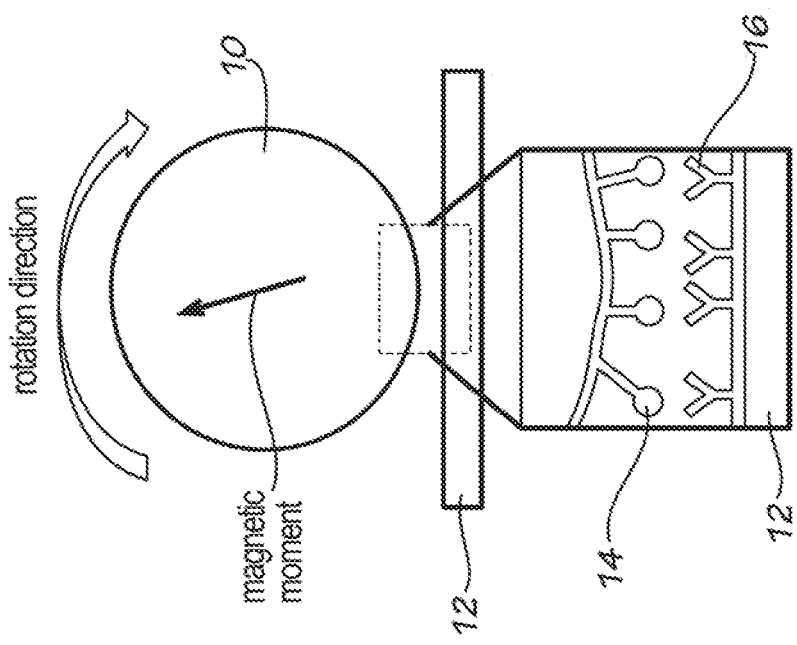

The mechanism by which the methods and systems provided herein operate can be further understood by reference to FIG. 1. As the magnetic beads 10 are exposed to a rotating magnetic field (not shown), the magnetic beads 10 rotate on/above the surface of the substrate 12. If the magnetic beads 10 have a surface with a given composition that includes one or more of a first type of molecule 14 (the "bead molecules") without any binding affinity for the one or more of a second type of molecule 16 (the "substrate molecules") on the surface of the substrate 12, no binding will occur at the interface of the rotating magnetic beads 10 and substrate 12, and the rotating magnetic beads 10 may move only a small distance when exposed to the rotating magnetic field (FIG. 1A). If the magnetic beads 20 have bead molecules 24 with a binding affinity for the substrate molecules 26 on the substrate 22, molecular bonds 28 (or "bridges") will form at the interface of the rotating magnetic beads 20 and the substrate 22 (FIG. 1B). The molecular bonds 28 result in an increase in friction, causing the rotating magnetic beads 20 to move more rapidly across the surface of the substrate 22 (i.e., increasing the translational velocity). Thus, the translational velocity of the rotating magnetic beads provides a direct mechanism by which to characterize the binding affinity between two different molecules.

The translational velocity of the rotating magnetic beads is a linear function of the number of bonds formed between the molecules on the magnetic beads and substrate when the system is below saturation. The number of bonds formed is a linear function of the concentration of free binding sites. Thus, the concentration of free binding sites is a linear function of the translational velocity. Because the frequency of rotation of the magnetic field regulates the saturation level of the translational velocity, a wide variety of interactions may be detected by modifying the magnitude and the frequency of the rotating magnetic field.

In embodiments, the translational velocity is modulated by adding one or more free molecules to the solution of rotating magnetic beads (FIG. 2). As used herein, "free molecules" are those that are not initially bound to the surface of either the magnetic beads or substrate and may be essentially any type of molecule, including those described below as being suitable for use as bead or substrate molecules. In embodiments, the free molecules 124 may comprise masking molecules capable of binding with the substrate molecules 128 on the substrate 126 (FIG. 2A). The free molecules 124 may interfere with the binding of the bead molecules 122 on the rotating magnetic beads 120 to the substrate molecules 128, reducing the translational velocity of the rotating magnetic beads to the limit in which only lubrication forces are important (i.e., the solution is saturated). Alternatively, the free molecules 134 may bind to the substrate molecules 138 on the substrate 136 to increase the number or strength of the interactions between the bead molecules 132 on the rotating magnetic beads 130 and substrate molecules 138 on the surface of the substrate 136, thereby increasing the translational velocity of the rotating magnetic beads (FIG. 2B).

Thus, embodiments of the methods provided herein advantageously allow for detection and quantification of the binding affinity between different compositions using a simple, robust, and versatile method. In embodiments in which it is desirable to detect whether there is any binding between two compositions, the translational velocity of the magnetic beads is compared to the translational velocity of one or more controls. An increase in the translational velocity indicates binding between compositions. In further embodiments, it may be desirable to quantify the binding affinity between the two compositions. For example, the binding constant may be deduced using either a label-free or label-based modalities from the translational velocity.

In a label-free mode, changes in the translational velocity can be measured (as a function of time) to allow for the quantification of the binding affinity using various masking techniques, as illustrated in FIG. 4. In such embodiments, it is desirable to precisely control the chemical composition of the beads 200 and the substrate 202. Thus, the system may be "tuned" by modifying the concentration of inactive/active molecules on the surfaces of one or both of magnetic beads 200 or substrate 202.

Figure 4A:
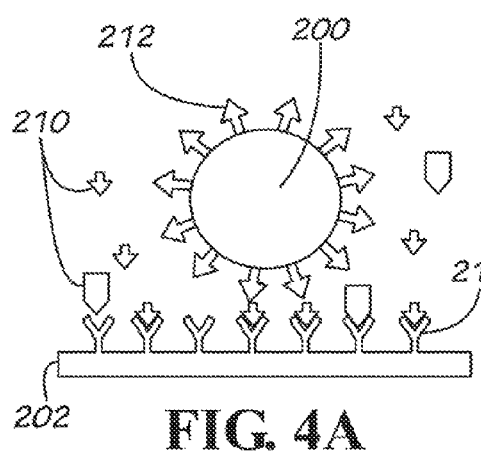
FIGS. 4A-4F are schematic illustrations of various techniques that may be used for quantification of binding affinity, including masking the substrate molecules (4A), masking the bead molecules (4B), masking both the substrate molecules and bead molecules (4C), association of a combination of free molecules with the bead and substrate molecules (4D), a dynamic system with the substrate comprising a cell (4E), and a dynamic system with a substrate comprising a decorated lipid bilayer (4F).
Figure 4B:
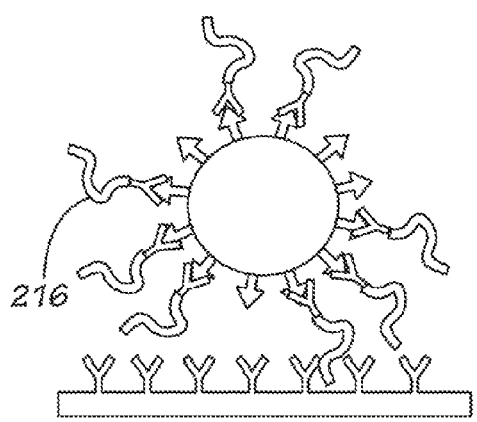
Figure 4C:
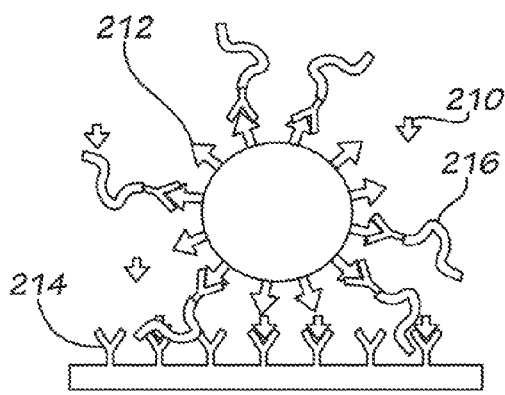
Figure 4D:
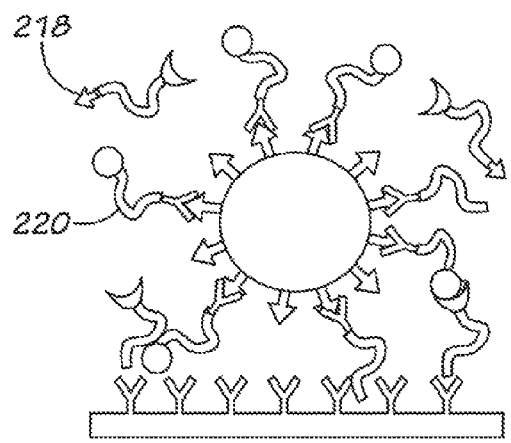
Figure 4E:
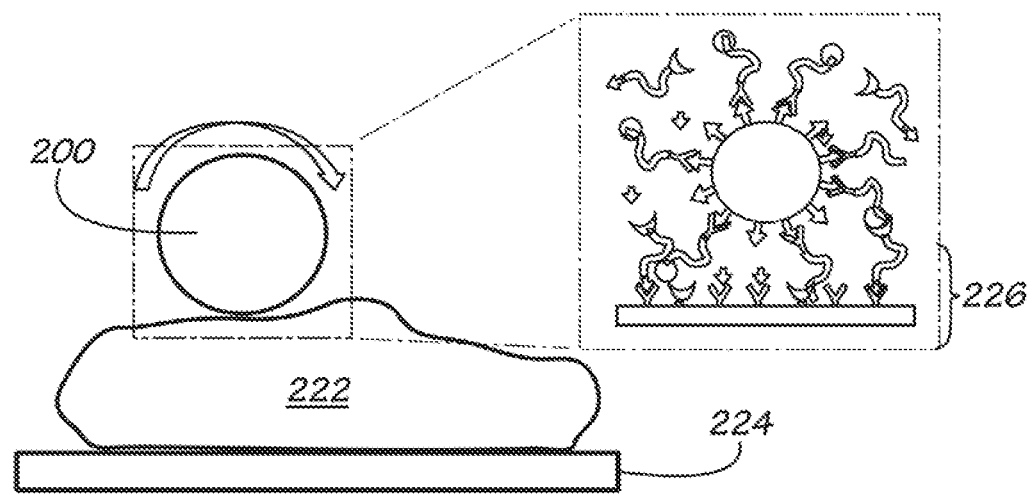
Figure 4F:
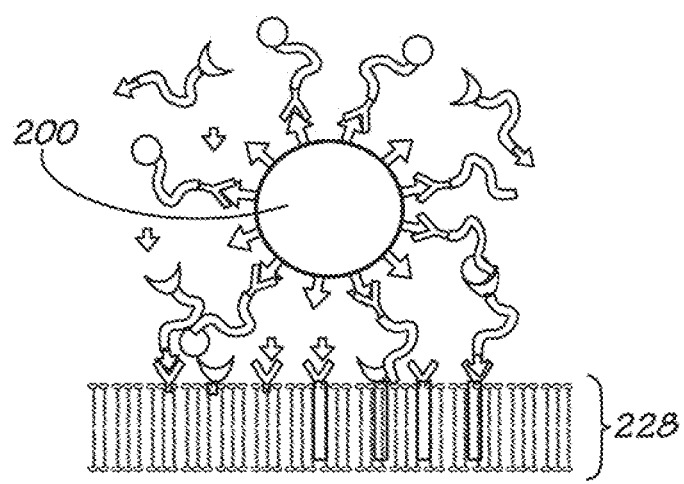

For example, as illustrated in FIG. 4A, masking can be achieved by addition of free molecules 210 that are active (e.g., free ligands) that mask the substrate molecules 214 (e.g., receptors) by interfering with the binding between the bead molecules 212 and the substrate molecules 214. By continuously measuring the translational velocity upon addition of the free molecules 210, the binding constant can be deduced by fitting the translational velocity curves as a function of time to an exponential or series of exponentials since the change in translational velocity is proportional (or inversely proportional) to the density of masked molecules. In another embodiment, illustrated in FIG. 4B, masking can be achieved by binding inactive molecules 216 (e.g., polyethylene glycol (PEG)) to a portion of the bead molecules 212, thereby diluting the number of possible binding sites. Again, by continuously measuring the translational velocity upon dilution of the binding sites, the binding constant can be deduced. In another embodiment, illustrated in FIG. 4C, a combination of the above-described masking techniques is provided by masking a portion of the bead molecules 212 with inactive molecules 216 and adding free molecules 210 to interfere with binding between the bead molecules 212 and substrate molecules 214. In still another embodiment, illustrated in FIG. 4D, a combination of free molecules 218, 220 (i.e., free bridging molecules) may be added that bind to one or more of the bead molecules 212, or substrate molecules 214, or other free molecules 218, 220. The foregoing techniques also may be utilized in complex systems, as illustrated in FIGS. 4E and 4F, in which a bead 200 is shown rolling on a dynamic cell surface 222 (4E) or a decorated lipid bilayer 228 (4F). The cell 222 may be fixed on a cell substrate 224 having one or more substrate molecules 214 on its cell membrane 226 that bind to one or more of the bead molecules 212 or free molecules 210, 218, 220. Similarly, a lipid bilayer 228 may be standing on a solid substrate or of the supported type with a polymer layer in-between the substrate and the lipid bilayer. For example, the lipid bilayer may be a decorated lipid bilayer comprising lipids and other molecules 214. In either case, the substrate molecules 214 bound to the lipid bilayer 228 bind to one or more of the bead molecules 212 or free molecules 210, 218, 220.

Quantification of the binding affinity can also be performed using label-based modalities to determine the binding constant. For example, the rotation frequency of the magnetic beads may be modified until no binding is observed between the bead molecules and substrate molecules. In such embodiments, an effective association constant can be determined by multiplying the concentration of the bead molecules by the critical frequency at which no binding is observed between the bead molecules and substrate molecules.

A. Magnetic Beads, Substrates, and Molecules

The magnetic beads, as used herein, include magnetic beads and chains of one or more magnetic beads. The magnetic beads may be permanent magnets, paramagnetic, or super-paramagnetic, and are commercially available in a variety of sizes and with a variety of different surface chemistries. The magnetic beads have a surface comprising one or more of a first type of composition, such as a first type of molecule (the "bead molecules"). The type and concentration of the bead molecules may be precisely controlled. For example, the bead molecules may actively bind to the substrate molecules while one or more free molecules may bind to a portion of the bead molecules. Alternatively, the magnetic beads may further comprise one or more of a third type of composition, such as a third type of molecule (the "third molecules") or any additional number of different types of molecules, on its surface (i.e., not necessarily bound to any of the bead molecules). In either case, the free molecules or third molecules may be inactive (i.e., not binding to the substrate molecules) to dilute the concentration of active binding sites on the surface of the magnetic beads. Alternatively, the free molecules or third molecules may increase the interactions between the bead molecules and substrate molecules.

In an embodiment, one or both of the substrate and the magnetic beads are functionalized with a complex, dynamic system, such as cells or another biological structure. Examples of such embodiments are illustrated in FIGS. 4E and 4F, described hereinabove.

The magnetic beads may be selected such that the size of the magnetic beads are sufficiently large to (i) be optically detected; (ii) have sufficient binding sites relative to the average the number of interactions; and (iii) contain sufficient magnetic material to respond to a rotating magnetic field. Generally, the magnetic beads may have a diameter from about 10 nm to about 100 µm. For example, magnetic beads having a diameter of at least 0.5 µm can be easily detected using conventional optical detectors, such as microscopes. In embodiments the magnetic beads have a diameter from about 0.5 µm to about 100 µm, from about 0.5 µm to about 50 µm, from about 1 µm to about 25 µm, or from about 1 µm to about 10 µm.

The substrate may be fixed or dynamic composition. In one embodiment, the substrate consists essentially of a single composition, such as a single molecule type. In another embodiment, the substrate comprises two or more compositions, such as two or more types of molecules. An example of a dynamic, or variable, composition is one which comprises cells coating the surface. The substrates used in the methods and systems provided herein may be formed from a variety of different materials to which one or more of the second type of molecules (the "substrate molecules") are immobilized.

Desirably, the substrate is sufficiently larger in size than the magnetic beads to permit movement of the magnetic beads without interference. For example, in embodiments the substrate has a length of at least about 500 μm, but may still be sufficiently small to permit measuring of a multitude of different parameters using a single slide. For example, in embodiments the substrate may be modified or unmodified microwell plates, non-limiting examples of which include microwell plates having 96 or more microwells. The substrate may be planar; however, it is not required, as long as the radius of curvature of the surface and/or non-planar surface features do not unduly impede translation of the magnetic beads.

Advantageously, the large number of interactions that may be present between a magnetic bead and the substrate provides significant amplification of the signal in systems and methods provided herein. The area per molecule on both surfaces can approach 100 $nm^2$, which is very small area compared to the actual area of interaction between the surfaces, which is on the order of $10^4$ $nm^2$. Thus, in those systems in which there are few interacting sites, the probability of there being binding is still large, enabling measurement of very weak interactions, such as salt bridges.

The type of compositions on the magnetic beads and substrate may be biological or synthetic in origin, organic or inorganic. In embodiments, the compositions comprise molecules that are independently selected from proteins, nucleic acids, glycoproteins, carbohydrates, or hormones. Non-limiting examples of pairs of bead and substrate molecules that may be used on the magnetic beads and substrate include antibody-antigen pairs; ligand-receptor pairs; enzyme-inhibitor pairs; protein-DNA pairs; protein-RNA pairs; two different carbohydrates; two different DNAs; and two different peptides. Non-limiting, other organic or inorganic molecules also can be considered, such as PEG, metal-coordination complexes, charged molecules (e.g., charged ligands), and the like. In embodiments, the molecules may comprise small molecules (i.e., a compound having a molecular weight below 800 Daltons and a size on the order of $10^{-9}$ m). In other embodiments, the molecules may comprise biopolymers that may be formed from constituent monomers comprising small molecules. Thus, a variety of different types of molecular interactions may be evaluated using the systems and methods described herein.

The compositions may be bound directly to the surface of the magnetic beads or substrates or to a coating on the surface of the magnetic beads or substrates that modifies its surface chemistry. For example, magnetic beads are commercially available with surfaces having amine groups, carboxylic acid groups, biotin, or streptavidin coated surfaces. The binding affinity of the magnetic bead can then be modified by attaching one or more compositions to the available chemical groups, providing a simple mechanism for creating concentration gradients for detection, measurement, and quantification of binding using a variety of different approaches. Essentially any surface chemistry with any type of binding group(s) can be used with the presently disclosed methods and systems.

The compositions/surface chemistries described herein may be configured for use on either the magnetic bead or the substrate surface. In other words, the bead and substrate molecules can be reversed and the methods and systems remain operable.

B. Systems to Measure Binding Affinity

Systems for measuring the binding affinity of different compositions are also provided. Such systems generally include a magnetic field source configured to apply a rotating magnetic field to magnetic beads in contact with a substrate, an optical detector, and a processor coupled to the optical detector. In a preferred embodiment, the optical detector includes an optical microscope which uses visible light. In other embodiments, other types of optical detectors may be used, non-limiting examples of which include fluorescence microscopy and super resolution microscopy.

In an alternative embodiment, non-optical detectors may be used. Examples of these include magnetic resonance imaging (MRI) and magnetic detectors.

Figure 3:
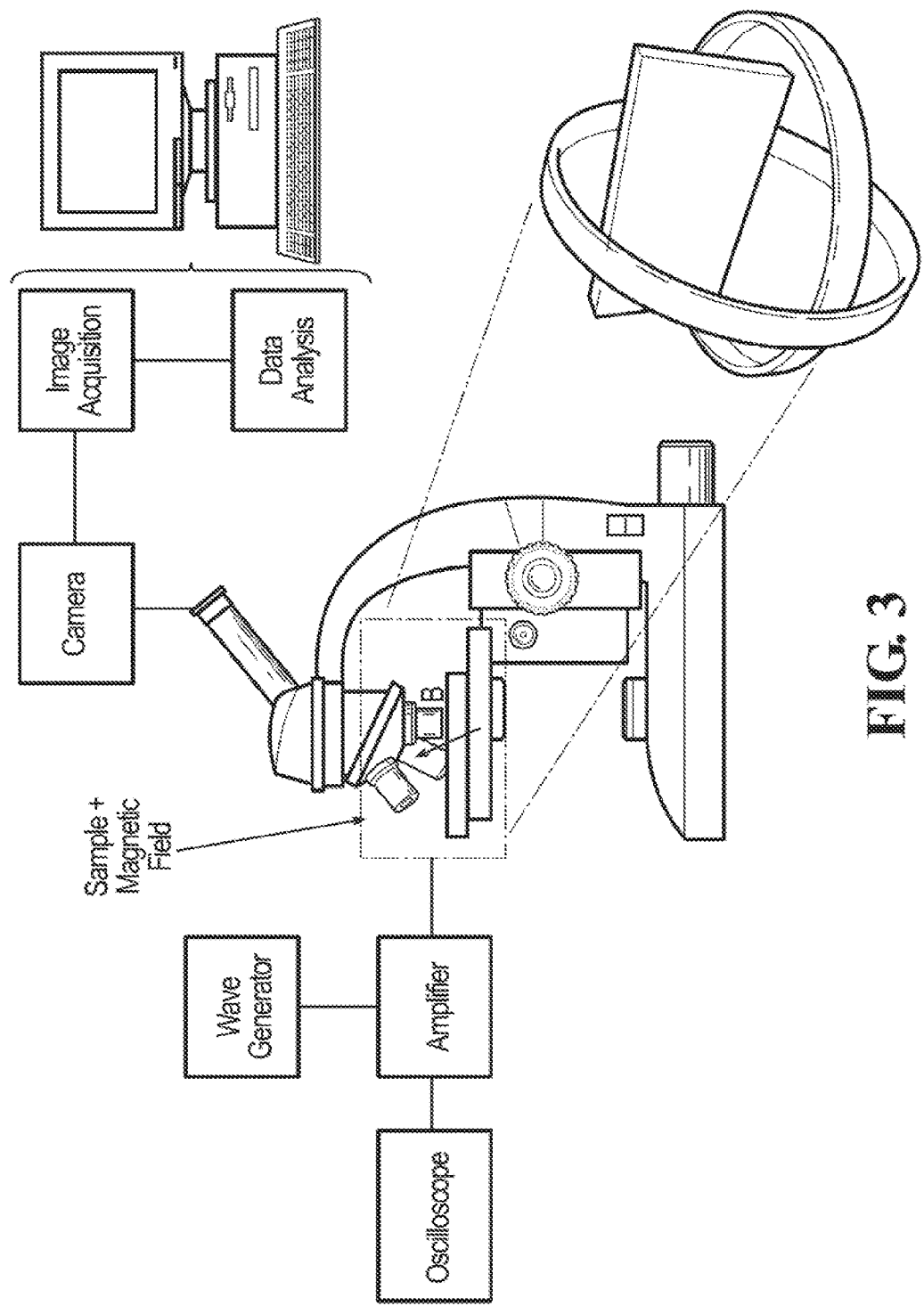
FIG. 3 is a schematic of a system for measuring the binding affinity of different molecules according to an embodiment.

In an exemplary system, illustrated in FIG. 3, the optical detector is a microscope that is coupled to a camera for capturing images of the rotating magnetic beads moving across the surface of the substrate. The camera is connected to the processor (typically a computer) that is configured to analyze the data and determine the translational velocity of the rotating magnetic beads. The processor also may be configured to provide qualitative analysis of whether or not there is a binding pair present or quantitative analysis of kinetic information, such as the binding constant. For example, the processor may be programmed with tracking algorithms to detect and measure the movement of the rotating magnetic beads across the surface of the substrate as a function of time. Such tracking algorithms are commercially available or can be customized by those in the art.

The driving force of the system is the magnetic field source that applies the rotating magnetic field. In embodiments, the magnetic field source includes a pair of crossed-coils, an amplifier, an oscilloscope, and a wave generator (FIG. 3). The magnetic field source may generate the rotating magnetic field by applying two sinusoidal currents shifted by 90 degrees through the coils. The rotating magnetic field, however, can be created using other configurations of coils, permanent magnets, or electromagnets. In embodiments, the magnetic field source is be configured to apply the rotating magnetic field in a plane that is parallel to the substrate while in other embodiments the magnetic field source is configured to apply the rotating magnetic field in a plane that is at an angle to the substrate.

Generally, the magnetic field will range from about 1 mT to about 500 mT, or more particularly from about 1 mT to about 200 mT. For example, a magnetic field generated by air or water chilled coils may range from about 1 mT to about 100 mT while that generated by permanent magnets or electromagnets may range up to 500 mT. Although stronger magnetic fields may be obtained using permanent magnets or electromagnets, such fields are not as uniform and could result in spurious drifts of the magnetic beads. Thus, coils are preferred as a magnetic field source, but may require use of magnetic beads having higher magnetic moments.

The magnetic moment of the magnetic beads (m) is calculated by:

$$m = \frac{V_c \Delta \chi}{\mu_0} B,$$

where $\mu_0$ is the magnetic permittivity, $V_c$ is the effective volume of the magnetic bead (that typically is superparamagnetic, but can be paramagnetic or permanently magnetic), $\Delta_\chi$ is the magnetic susceptibility difference between the magnetic bead and the medium (e.g., in the case of water, the difference is $\Delta_\chi$=0.7), and B is the magnetic field. The force $F_{B,ij}$ between two induced moments $m_i$ and $m_j$ is given by:

$$F_{B,ij} = \frac{3\mu_0}{4\pi r^4}\left(\begin{array}{c}\left(\frac{m_i \cdot r_{ij}}{r}\right)m_j + \left(\frac{m_j \cdot r_{ij}}{r}\right)m_i - \\ \left(\frac{5(m_j \cdot r_{ij})(m_i \cdot r_{ij})}{r^2} - (m_i \cdot m_j)\right)\frac{r_{ij}}{r}\end{array}\right)$$

where $r_{ij}$ is the position vector between beads i and j, with magnitude r. The torque T on a single magnetic bead with a permanent magnetic moment is simply:

$$T = m \times B$$

In the case of superparamagnetic beads (or quasi super paramagnetic beads), such torque is minimal because the magnetic material can reorient its dipoles to align with the field. On the other hand, in embodiments in which the magnetic beads are a chain of magnetic beads, the effective magnetic moment is $m_{chain} = Nm$, where N is the number of magnetic beads in the chain.

The typical force that these systems can apply may range from sub pN to 10 nN and will depend on both the magnetic field and the magnetic content of the magnetic bead. Typically, the lower end of the force applied may be characterized by smaller beads (~1 μm) and a magnetic field of the order of 1 mT, while the upper end of the force applied may be characterized by much larger beads (~100 μm) and a magnetic field on the order of 100 mT. In systems using larger beads, it may be necessary to control the friction generated by binding, which increases with the square of the size of the bead. For example, it may be desirable to include both the active and inactive molecules on the surface of the magnetic beads.

The present description is further illustrated by the following non-limiting examples.

Example 1

The system used in the experiments below is consistent with that illustrated in FIG. 3. A standard light microscope was used with mounted Helmholtz coils centered on the sample to produce a rotating magnetic field. A custom made wave generator ran two sinusoidal signals (one per coil), phase shifted by 90 degrees, to obtain the homogenous rotating magnetic field. The relatively small coils were chosen so that the Helmholtz coils would fit within the objective and the condenser in order to avoid any unwanted magnetic eddies that could be produced from the interaction of the magnetic field and the metal in the microscope. The sample stage was mounted externally so as not to be coupled to the coils.

The signal from the wave generator was passed through a Crown® amplifier (Harman International) before reaching the coils. A 300 W amplifier (150 W/channel) was enough to run sufficient current through more than 100 turns of wire. The field that was used throughout the following experiments was 100 Oe. The signal from the amplifier was routed to an oscilloscope in order to obtain a precise measurement of the frequency and the voltage at the output. Data acquisition was accomplished via a CCD camera that was mounted on the microscope, which used an objective lens of 40×. The camera was connected to a computer (Dell™) for visualization and video capture, the video was recorded on the computer, and a custom software program was used to track the movement of the magnetic beads and provide measurements of distance vs. time. This data was then further analyzed using, for example, Mathematica® for a more thorough and in-depth analysis of motion.

Example 2

Figure 5:
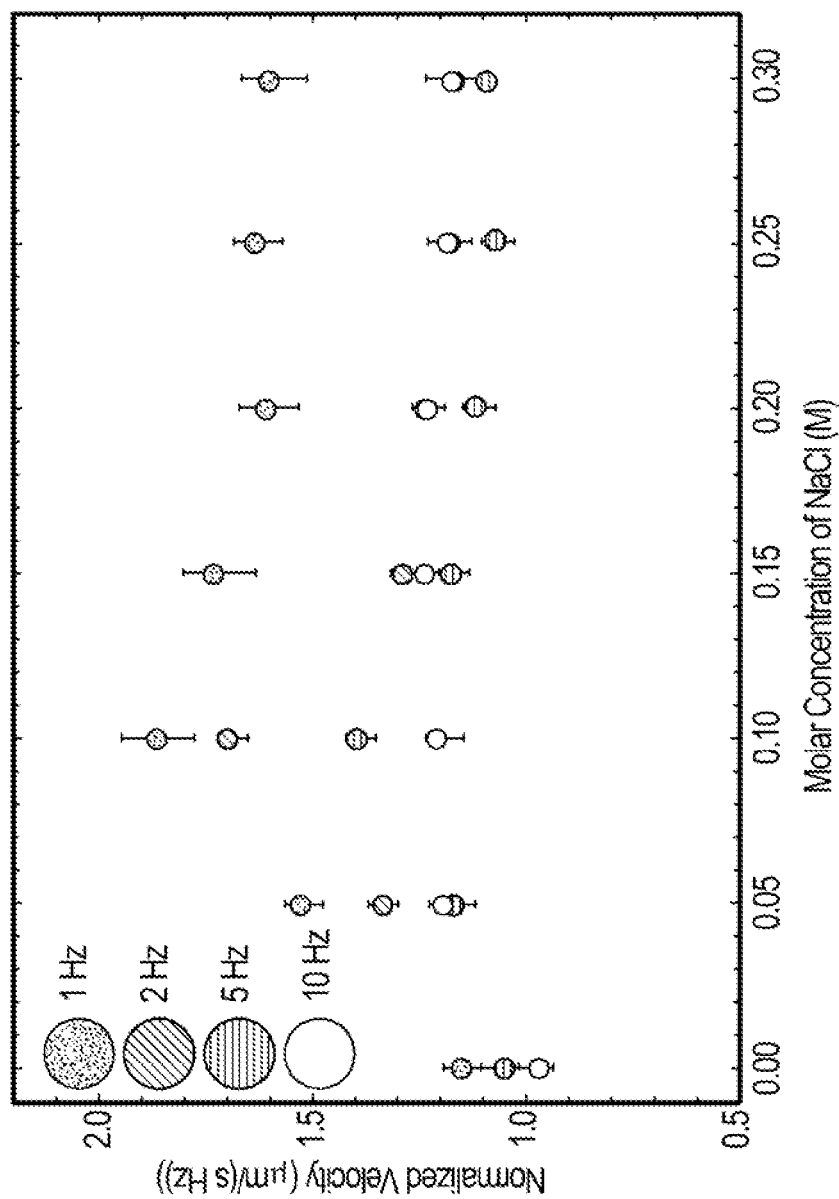
FIGS. 5-7 are plots of the normalized translational velocity of magnetic beads as a function of the amount of salt added to the system for sodium chloride (FIG. 5), lithium chloride (FIG. 6), or calcium chloride (FIG. 7).
Figure 6:
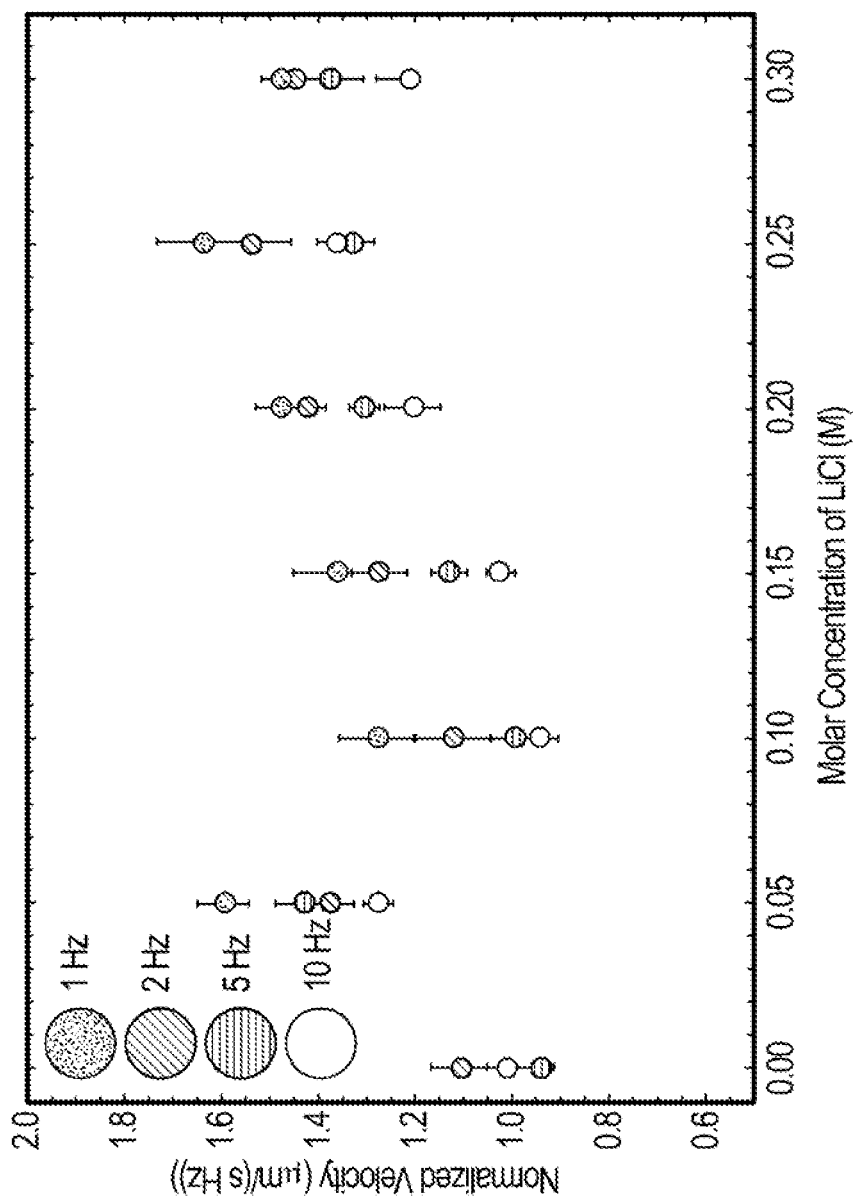
Figure 7:
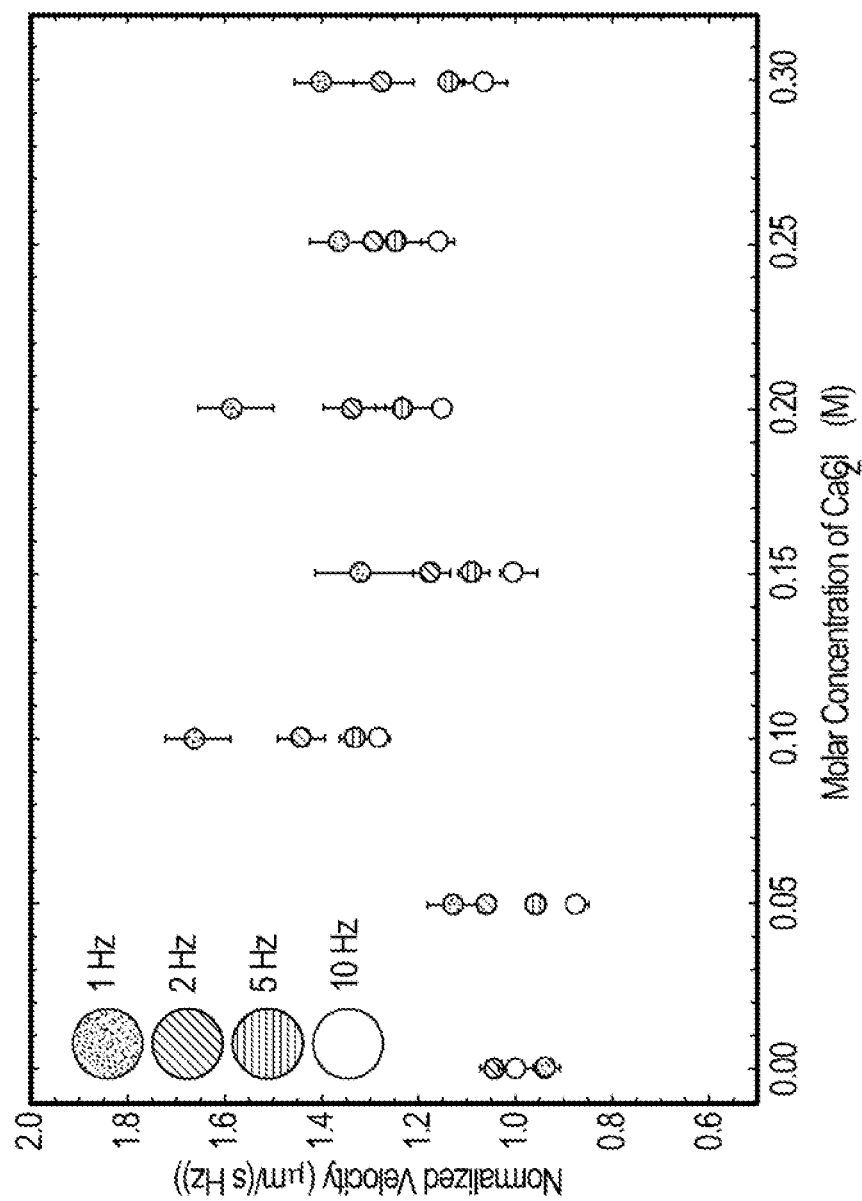

The measured normalized translational velocity of a magnetic bead doublet (i.e., a chain of two magnetic beads) was measured as a function of the amount of salt added to the system. Magnetic beads (Solulink™) with a diameter of 2.8 μm and a streptavidin coated surface were coated with biotinylated PEG chains having a molecular weight of 5000. The substrate was also coated with PEG molecules, creating a PEG brush. Salt was added and the translational velocity was measured at various concentrations using the system described in Example 1. The results are illustrated in FIGS. 5-7, which show the normalized translational velocity (v/frequency) as a function of the amount of salt added for sodium chloride, lithium chloride, or calcium chloride, respectively.

The methods permitted characterization of very weak and anomalous effects in the friction of PEG-coated surfaces in the presence of salt. Notably, the salt dependence was very different for each type of salt. For example, sodium chloride only exhibited one peak in the normalized translational velocity at intermediate concentrations, whereas both lithium chloride and calcium chloride exhibited two peaks. Although the cause of these differences is not fully understood, they are known in general as the salt anomalies of PEG. These anomalies suggest that PEG interacts with itself via salt bridges, and that these interactions are non-monotonic for most salts. Remarkably, the simple systems and methods described herein were capable of detecting such small forces.

Example 3

Chemotactic systems also were used to evaluate other applications for the methods and systems described herein using the magnetic beads described in Example 2 and system described in Example 1. A rotating magnetic field was used to drive the chains of magnetic beads to turn and walk on the surface of the substrate (i.e., a biased random walk). The substrate was prepared by creating a gradient medium on the substrate surface by drying a droplet containing avidin on a biotinylated surface of the substrate. The results are illustrated in FIGS. 8A and 8B.

Figure 8A:
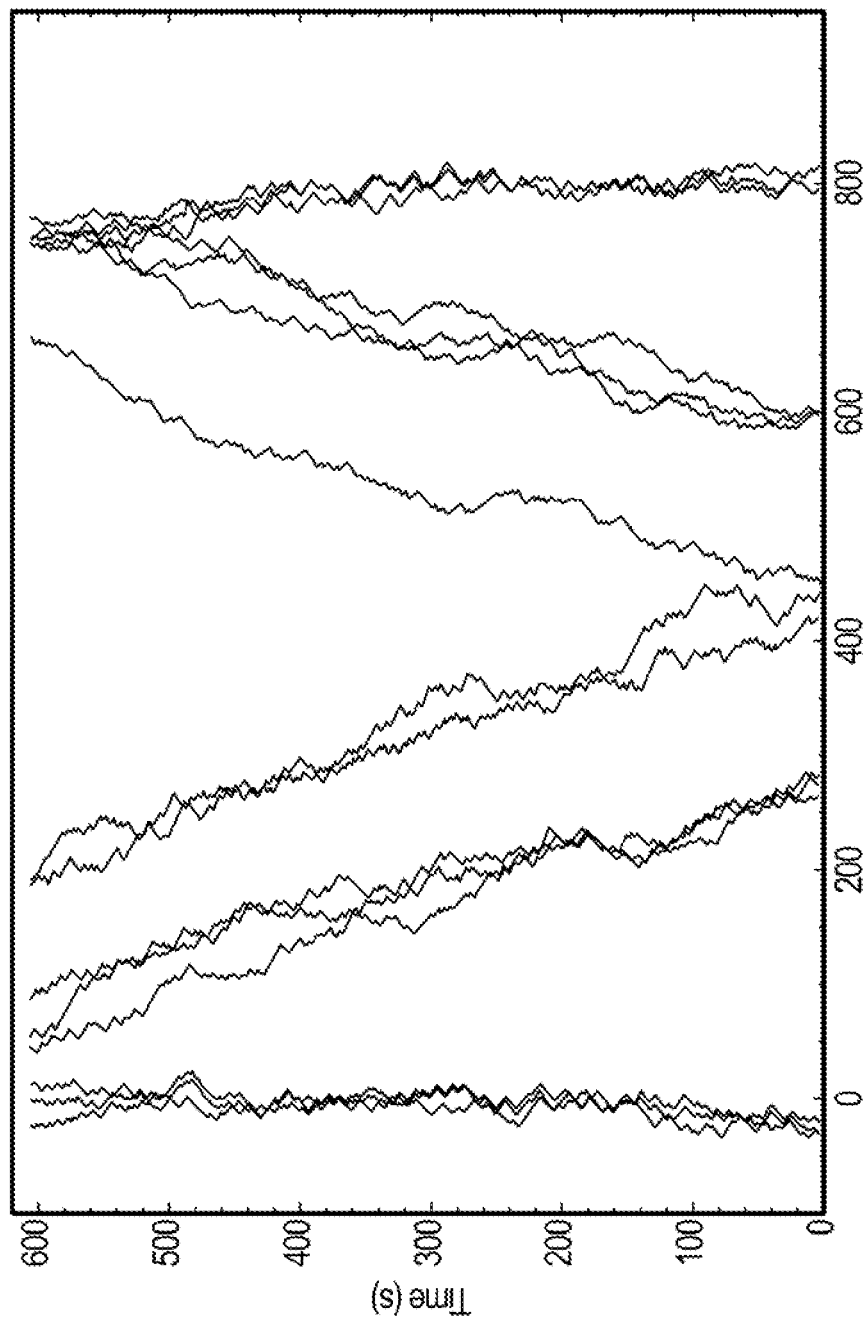
FIGS. 8A and 8B plot the movement over time (8A) and translational velocity (8B) as a function of time for magnetic beads with streptavidin molecules across a substrate formed by a droplet of avidin on a biotinylated surface.
Figure 8B:
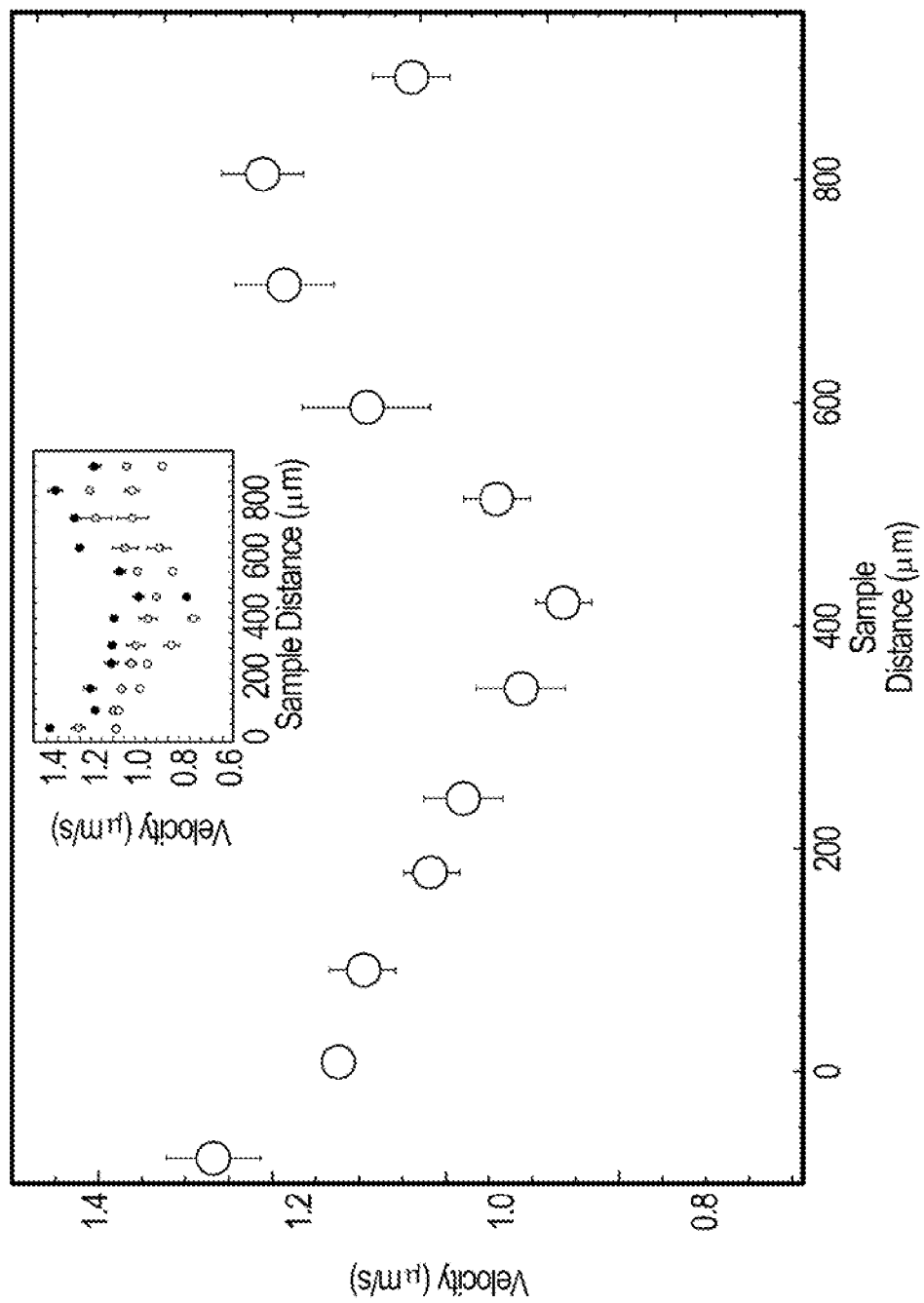

As shown in FIG. 8A, the streptavidin sites preferred to bind to the free biotin on the surface of the substrate, thus a larger velocity suggested a larger portion of free biotin molecules was present on the surface of the substrate. This was evident in the center of the droplet, from which bands formed in concentric rings with more or less coverage of avidin. Another band with more free biotin appeared at about 800 microns. As shown in FIG. 8B, a continuous run (no stochasticity) produced the greatest translational velocity at the origin and around 800 μm.

It is intended that the foregoing detailed description be regarded as illustrative, rather than limiting, and that it be understood that it is the following claims, including all equivalents, which are intended to define the scope of the invention.

We claim:

1. A method for detecting or measuring binding affinity between different compositions comprising:
   contacting one or more magnetic beads having a surface which comprises a first composition with a substrate having a surface which comprises a second composition, wherein the first composition differs from second composition;

applying a rotating magnetic field to the one or more magnetic beads effective to cause the one or more magnetic beads to move across the surface of the substrate;

measuring the movement of the one or more magnetic beads across the substrate surface to determine a translational velocity; and determining a quantitative binding affinity between the first and second compositions from the translational velocity.

2. The method of claim 1, wherein the step of determining the quantitative binding affinity comprises determining the affinity between the surface of the magnetic beads and the surface of the substrate.

3. The method of claim 1, wherein the step of measuring the translational velocity of the one or more magnetic beads is performed using optical microscopy.

4. The method of claim 1, wherein the step of determining the quantitative binding affinity comprises comparing the translational velocity of the one or more magnetic beads to the translational velocity of at least one control magnetic bead.

5. The method of claim 1, wherein the step of determining the quantitative binding affinity comprises calculating a binding constant.

6. The method of claim 1, further comprising contacting the one or more magnetic beads and substrate with free molecules.

7. The method of claim 1, wherein the first composition comprises a bound ligand and the second composition comprises a receptor, or the first composition comprises the receptor and the second composition comprises the bound ligand.

8. The method of claim 1, wherein the first composition comprises an antibody and the second composition comprises an antigen, or the first composition comprises the antigen and the second composition comprises the antibody.

9. The method of claim 1, wherein the first composition comprises an enzyme and the second composition comprises an inhibitor, or the first composition comprises the inhibitor and the second composition comprises the enzyme.

10. The method of claim 1, wherein the first composition comprises a protein and the second composition comprises a DNA, or the first composition comprises the DNA and the second composition comprises the protein.

11. The method of claim 1, wherein the first composition comprises a first DNA and the second composition comprises a second DNA.

12. The method of claim 1, wherein the first composition comprises a first peptide and the second composition comprises a second peptide.

13. The method of claim 1, wherein second composition comprises cells.

14. The method of claim 1, wherein the second composition comprises a lipid bilayer.

15. The method of claim 1, wherein:
the first composition comprises a first type of molecule, and the second composition comprises a second type of molecule; and
wherein the step of determining a quantitative binding affinity comprises determining the quantitative binding affinity between the first and second types of molecules.

16. The method of claim 15, further comprising contacting the first and second compositions with free molecules in an amount to affect the binding between the first and second types of the molecules.

17. The method of claim 15, wherein the first composition further comprises a substance which interferes with binding between the first and second type of molecules.

18. The method of claim 15, wherein the first composition further comprises a substance which increases binding between the first and second type of molecules.

19. The method of claim 15, wherein the first and second type of molecules are independently selected from the group consisting of proteins, nucleic acids, glycoproteins, carbohydrates, and hormones.

20. The method of claim 1, wherein the diameter of the magnetic beads is from 10 nm to 100 µm and the substrate surface has a length of at least 500 µm.

21. A method for determining the binding constant between two different molecules, comprising:
using the method of claim 1 with a target molecule and a substrate molecule under different conditions of at least one of the concentration of the target molecule in the first or second composition, the magnitude of the magnetic field, and the frequency of rotation of the magnetic field, to obtain at least one translational velocity curve; and
calculating a binding constant from the at least one translational velocity curve.

* * * * *